United States Patent [19]

Novotny et al.

[11] 4,126,752

[45] Nov. 21, 1978

[54] HOMOLOGATION OF METHANOL WITH A CARBON MONOXIDE-WATER MIXTURE

[75] Inventors: Miroslav Novotny, Denville; Lowell R. Anderson, Morristown, both of N.J.

[73] Assignee: Allied Chemical Corporation, Morris Township, Morris County, N.J.

[21] Appl. No.: 883,541

[22] Filed: Mar. 6, 1978

[51] Int. Cl.$^2$ ............................................. C07C 29/00
[52] U.S. Cl. ................................................ 568/902
[58] Field of Search ........................................ 568/902

[56] References Cited

U.S. PATENT DOCUMENTS

| | | | |
|---|---|---|---|
| 2,623,906 | 12/1952 | Gresham | 568/902 |
| 3,248,432 | 4/1966 | Riley et al. | 568/902 |
| 3,285,948 | 11/1966 | Butler | 568/902 |

FOREIGN PATENT DOCUMENTS 733,792  7/1955  United Kingdom.

OTHER PUBLICATIONS

Laine et al., "J. Am. Chem. Soc.," 99 (1), pp. 252-253, (1977).
Cheng et al., "J. Am. Chem. Soc.," 99 (8), pp. 2791-2792, (1977).

*Primary Examiner*—Joseph E. Evans
*Attorney, Agent, or Firm*—Robert J. North; Robert A. Harman

[57] ABSTRACT

An improved process is described for converting methanol to ethanol in which a mixture of methanol, liquid water and a Group VIII metal catalyst and a basic inorganic compound is contacted with an atmosphere of carbon monoxide at a temperature of about 240° to 280° C and a pressure of about 3,000–5,000 psi gauge. Good yields and selectivities of ethanol are obtained eliminating the necessity of using gaseous hydrogen or steam as starting materials, as required in prior art processes.

13 Claims, No Drawings

HOMOLOGATION OF METHANOL WITH A CARBON MONOXIDE-WATER MIXTURE

BACKGROUND OF THE INVENTION

1. Field of the Invention

This invention relates to an improved process for converting methanol to ethanol in which a liquid mixture of methanol, water, a Group VIII metal catalyst and a basic inorganic compound is contacted with an atmosphere of carbon monoxide at elevated temperature and pressure.

2. Brief Description of the Prior Art

Ethanol is a well known organic chemical and has a wide variety of industrial applications including use as a solvent for resins, fats and fatty acids and serves as a "building block" for the synthesis of a variety of larger molecular weight organic compounds.

The overall process of converting an organic compound to a higher homologue, by increasing the number of $CH_2$ units by one, is termed in the art, "homologation".

Processes for homologating methanol to ethanol are known in the art and provide a potential basis for the synthetic production of ethanol to supplement ethanol obtained by fermentation.

However, these processes, as illustrated in the references: Science, Vol. 113, pp. 206–207 (1951); British Pat. No. 951,506 (1964); U.S. Pat. No. 3,248,432 (1966); U.S. Pat. No. 3,285,948 (1966); U.S. Pat. No. 3,356,734 and Belgian Pat. No. 842,430, involve methods of homologating methanol in which gaseous mixtures of carbon monoxide and hydrogen gas are utilized. A method that does not require the use of hydrogen gas, a potentially explosive material, would be highly desirable.

A related reference, "Proceedings of the Symposium on Chemicals and Oil From Coal," Central Fuel Research Institute, June 1972, pages 151 to 158, describes the hydrogenation of coal in the presence of carbon monoxide, water and an inorganic base, such as sodium carbonate, in which a variety of hydrogenated organic products are obtained. However, the process is not described as being effective for producing ethanol in good yield and selectivity.

Another reference, British Pat. No. 733,792 (1955) describes a process in which methanol can be homologated to ethanol by passing a mixture of methanol and steam over a cobalt-thorium-copper heterogeneous catalyst at a pressure of about 100 atmospheres and a temperature of about 200° C. However, the process requires steam as a reactant, and the attendant requirements for its production, for producing a hydrogen source in the reaction.

SUMMARY OF THE INVENTION

We have unexpectedly found that ethanol can be produced in good yield and selectivity by homologating methanol in a mixture of water, a Group VIII metal catalyst and a basic inorganic compound under an atmosphere of carbon monoxide, at a pressure of about 3,000 to 5,000 psi gauge and a temperature of about 240° to 280° C. The process requires the presence of a basic inorganic compound and is conducted with liquid water rather than steam.

In accordance with this invention there is provided an improved process for converting methanol to ethanol including contacting a mixture of methanol, water and a Group VIII metal catalyst with an atmosphere consisting essentially of carbon monoxide, at a pressure greater than one atmosphere, wherein the improvement comprises conducting the process in the presence of a basic inorganic compound and at a temperature below the critical temperature of water, said water being substantially in the liquid state.

DETAILED DESCRIPTION OF THE INVENTION AND THE PREFERRED EMBODIMENTS

The overall process of this invention can be represented by the following equation:

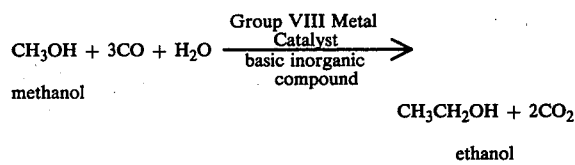

$$CH_3OH + 3CO + H_2O \xrightarrow[\text{basic inorganic compound}]{\text{Group VIII Metal Catalyst}} CH_3CH_2OH + 2CO_2$$

methanol → ethanol wherein water in the process is substantially in the liquid state.

The novelty of the present invention process is the discovery that methanol can be homologated to ethanol in good yield and selectivity in the presence of liquid water and a basic inorganic compound. Thus, the necessity of using steam as a reactant, coupled with the high energy requirements for its production, as practiced in the above-identified prior art, is eliminated. The reason that the homologation of methanol to ethanol occurs in liquid water in the presence of a basic inorganic compound is not clearly understood. It is thought that the basic inorganic compound catalyzes the formation of an intermediate salt of an organic compound, possibly sodium formate, which in turn generates nascent hydrogen in the process required for the homologation reaction. By eliminating the necessity of using steam or hydrogen as starting reactants, the present invention process thus represents a significant advance in the state of the art in which ethanol, from which larger and more complex organic compounds may be obtained by other processes, can be produced via the homologation of methanol in the presence of available inexpensive starting materials.

By the term "basic inorganic compound", as used herein, is meant a solid inorganic compound, including a salt, which dissolves in water, or reacts with water to produce another basic inorganic compound that dissolves in water, thus producing an alkaline aqueous medium, i.e. of a pH above 7.0.

Included among basic inorganic compounds applicable in the process are compounds containing alkali and alkaline earth metal cations and including anions such as oxides, hydroxides, carbonates and bicarbonates. Representative examples of basic inorganic compounds include sodium hydroxide, sodium bicarbonate, sodium carbonate, sodium oxide, potassium hydroxide, potassium bicarbonate, potassium carbonate, lithium hydroxide, lithium carbonate, magnesium oxide, magnesium hydroxide, magnesium carbonate, calcium hydroxide, sodium formate, potassium formate, sodium acetate, potassium acetate and the like.

A preferred class of basic inorganic compounds are those containing alkali and alkaline earth metal cations and carbonate anions. Especially preferred in the process are the basic inorganic salts, sodium and potassium carbonate.

The amount of basic inorganic compound that is used in the process is generally in the amount of about 0.01 to 0.5 parts of basic inorganic compound per part of methanol and preferably about 0.1 to 0.3 parts of basic inorganic compound per part of methanol. Preferably, the basic inorganic compound is soluble in the mixture of methanol, water and Group VIII metal catalyst.

The temperature used in the process, i.e., the reaction temperature, is a temperature below the critical temperature of water, i.e. 374° C., such that the water reactant in the process is substantially in the liquid state at the particular pressure used in the process. By the term "substantially in the liquid state" is meant to include water vapor but not steam. Preferably, a temperature range of about 240° to 270° C. is used in the process and particularly preferred is a temperature range of about 260° to 270° C. However, temperatures lower than 240° may also be employed if mixtures of Group VIII catalysts are used.

The water reactant substantially in the liquid state in the invention process is usually used in an amount of about 0.1 to 2.0 parts per part by weight of methanol.

Carbon monoxide reactant is contacted with the mixture of methanol, water, basic inorganic compound and Group VIII metal catalyst at a pressure greater than atmospheric, and allowed to react with said mixture at the reaction temperature i.e. below the critical temperature of water.

Preferably, the atmosphere above the reaction mixture is substantially carbon monoxide although up to about 10 volume percent of other gases may also be present such as air, hydrogen, carbon dioxide and the like at the beginning of the process. During the process, the atmosphere in contact with the mixture of methanol, water, basic inorganic compound, Group VIII metal catalyst, may be evacuated and replaced by a fresh charge of carbon monoxide to increase percent methanol conversion and/or selectivity for ethanol. Sufficient carbon monoxide in the process, should be present such that at least the stoichiometric molar ratio, 3:1 carbon monoxide/methanol, is present.

Group VIII metal catalysts useful in the reaction include compounds and salts containing cobalt, iron, rhodium, ruthenium and the like or mixtures thereof and representative examples include dicobalt octacarbonyl, cobalt acetate and hydrates thereof, cobalt halides, such as iodides, cobalt carbonate and cobalt oxide, particularly fused onto an inert carrier or substrate such as silicon dioxide. Preferred are cobalt-containing catalysts. The Group VIII metal catalyst can be soluble or insoluble in the mixture of methanol, water and basic inorganic compound. Generally, an amount of Group VIII metal catalyst of about 0.01 to 0.5 parts per part of methanol is used in the process.

The process is conducted under a pressure of about 3000 to 5000 psi gauge, at the reaction temperature, of an atmosphere of carbon monoxide, and preferably at a pressure of about 4500 to 5000 psi gauge.

Secondary reagents, acting as promoters, can also be utilized in the reaction as an aid in increasing the percent conversion of methanol, or the rate of said conversion obtained in the process. The reagents should be soluble in the reaction medium and should not chemically react with product ethanol under the reaction conditions. Representative examples of promoter reagent include halides of alkali and alkaline earth metals such as sodium bromide, sodium iodide, potassium bromide, potassium iodide, lithium bromide, lithium iodide, calcium iodide, magnesium iodide, sodium chloride, sodium fluoride, and iodine, and organic halides, such as $C_1$–$C_4$ alkyl iodides such as ethyl iodide and the like, and mixtures thereof. The amount of promoter agent usually used is about 0.005 to 0.1 parts of promoter reagent per part of methanol.

The yields of ethanol in the process are usually in the range of about 10 to 25 percent based on the number of moles of methanol introduced into the process.

The selectivity for ethanol produced in the process is defined as (moles ethanol formed ÷ moles of methanol converted) × 100 and the selectivities are generally in the range of about 20 to 40 percent.

Byproducts in the process usually include methyl acetate, methyl formate, 1,1-dimethoxyethane, acetaldehyde, ethyl acetate, and small amounts of higher alcohols and their esters. Pure ethanol can be obtained and recovered in the process by conventional techniques such as subjecting the reaction mixture to conventional distilling procedures. Byproducts produced in the process which can be separated from product ethanol can also be identified by combined gas chromatography and mass spectroscopy techniques.

Included among apparatus useful in carrying out the invention process are conventional pressure reactor apparatus with means for agitation or rocking, means for heating, means for degassing and means for introducing a gaseous mixture, such as carbon monoxide under pressure during the process run.

The following examples are illustrative of the best mode of the carrying out the invention, as contemplated by us, but should not be construed to be limitations on the scope or spirit of the instant invention. Parts are by weight where given unless otherwise indicated.

EXAMPLE 1

Into a 183 ml (316 SS) rocker reactor were charged 0.34 gram (1.0 millimole) dicobalt octacarbonyl, 13.8 grams (0.43 mole) methanol, 15.0 grams (0.83 mole) water, 3.0 grams (28 millimoles) sodium carbonate and 0.25 grams (1.7 millimoles) sodium iodide. The reactor was purged several times with carbon monoxide (Matheson Gas Products ®, UHP), and the reaction mixture was pressurized with carbon monoxide to a pressure of 2,600 psi gauge, at room temperature, and the contents agitated by rocking at 260° C. for 4 hours, during which the internal pressure was about 4600 psi gauge maximum. After cooling, the gaseous products were analyzed by a Hewlett-Packard 5710A gas chromatograph and were found to consist of 69% carbon monoxide, 13% hydrogen and 18% carbon dioxide by volume. The liquid products were analyzed by a combined gas chromatography-mass spectrometry technique and the main fractions were separated by distillation. The results indicated that 42% of methanol was converted, ethanol was formed in 29% selectivity, methyl acetate was formed in 14% selectivity, and 1,1-dimethoxyethane was formed in 7% selectivity. A solid residue, which was isolated by distilling away the liquid products, was found to be sodium acetate partially contaminated with sodium formate. When this was included in the product distribution, more than 80% of the starting methanol could be accounted for. Other minor products which were observed included methyl formate, acetaldehyde and ethyl acetate. Methane was not detected.

COMPARATIVE TEST

The same procedure and apparatus described in Example 1 was carried out except a basic inorganic salt was not used. After the reaction, the results indicated that methyl acetate and acetic acid were the only major products.

EXAMPLE 2

Utilizing the procedure and apparatus of Example 1, but varying the nature and amount used of the Group VIII metal catalyst additional runs were made, the results of which are tabulated below in Table I (including Example 1 as Run 1).

TABLE I
Influence of Different Group VIII Metal Catalysts on the Homologation of Methanol

| Run | Catalyst | $C_{MeOH}$ (%)[c] | $S_{EtOH}$ (%)[d] | $S_{MeOAc}$ (%)[e] |
|---|---|---|---|---|
| 1 | 0.34 gm of $Co_2(CO)_8$ | 42 | 29 | 14 |
| 2 | 0.25 gm of $Co(OAc)_2 \cdot 4H_2O$ | 49 | 21 | 16 |
| 3 | 0.05 gm of $Co(OAc)_2 \cdot 4H_2O$ | 37 | 18 | 16 |
| 4 | 0.31 gm of $CoI_2$ | 50 | 23 | 24 |
| 5 | 0.12 gm of $CoCO_3$ | 37 | 25 | 20 |
| 6 | 0.5 gm of $CoO/SiO_2$[a] | 29 | 27 | 13 |
| 7 | 0.5 gm of $CoO/SiO_2$[b] | 52 | 38 | 14 |

[a] Harshaw cobalt catalyst, Co-0403 G4-8.
[b] The reaction mixture was cooled after the first 4 hours, the gases were vented, the mixture was re-pressurized with a fresh charge of carbon monoxide (2600 psi) and the reaction carried out for another 4 hours at 260° C.

[c] $C_{MeOH} = \frac{\text{moles methanol converted}}{\text{moles methanol introduced}} \times 100$

[d] $S_{EtOH} = \frac{\text{moles ethanol formed}}{\text{moles methanol converted}} \times 100$

[e] $S_{MeOAc} = \frac{\text{moles methyl acetate formed}}{\text{moles methanol converted}} \times 100$

EXAMPLE 3

Utilizing the apparatus of Example 1, 0.5 gram of $CoO/SiO_2$ catalyst, 13.8 grams (0.43 moles) of methanol, 15.0 grams (0.83 moles) of water, 3.0 grams (28 mmoles) of sodium carbonate and 0.25 gram (1.7 mmoles) of sodium iodide were charged into the 183 ml (316 SS) rocker reactor. After purging the reaction several times with carbon monoxide the reaction mixture was pressurized with 2600 psi of CO at room temperature and rocked at the given temperature for 4 hours. After cooling, the gaseous and liquid products were analyzed in the usual manner. The results, in the temperature region from 240° C. to 270° C., are presented below in Table II. Further increase of the temperature above 270° C. was found to have a negative effect on the methanol conversion, as well as the yield of the produced ethanol. Where identical, the headings in Table II are the same as in Table I.

TABLE II
The Influence of Temperature on Methanol Homologation with $CO/H_2O$ Mixtures

| t [°C] | $C_{H_2O}$ [%][f] | $C_{MeOH}$ [%] | $Y_{EtOH}$ [%][g] | $Y_{MeOAc}$ [%][h] |
|---|---|---|---|---|
| 240 | 4 | 22 | 3 | 4 |
| 250 | 6 | 22 | 3 | 4 |
| 255 | 10 | 28 | 6 | 4 |
| 260 | 18 | 29 | 8 | 3 |
| 270 | 23 | 27 | 8 | 2 |

[f] $C_{H_2O} = \frac{\text{moles water converted}}{\text{moles water}} \times 100$

[g] $Y_{EtOH} = \frac{\text{moles ethanol produced}}{\text{moles methanol in starting mixture}} \times 100$

[h] $Y_{MeOAc} = \frac{\text{moles methyl acetate produced}}{\text{moles methanol in starting mixture}} \times 100$

We claim:

1. In a process for converting methanol to ethanol including contacting a mixture of methanol, water and Group VIII metal catalyst with an atmosphere consisting essentially of carbon monoxide, at a pressure greater than one atmosphere, the improvement which comprises conducting the process in the presence of a basic inorganic compound and at a temperature below the critical temperature of water, said water being substantially in the liquid state.

2. The improvement in accordance with claim 1 wherein said basic inorganic compound is an alkali metal or alkaline earth metal inorganic basic compound.

3. The improvement in accordance with claim 2 wherein said basic inorganic compound is an alkali metal or alkaline earth metal carbonate.

4. The improvement in accordance with claim 3 wherein said basic inorganic compound is sodium or potassium carbonate.

5. The improvement in accordance with claim 1 wherein said basic inorganic compound is soluble in the mixture of methanol, water and Group VIII metal catalyst.

6. The improvement in accordance with claim 1 wherein the temperature of the process is about 240° to 280° C.

7. The improvement in accordance with claim 1 wherein the pressure of the carbon monoxide atmosphere is about 3,000 to 5,000 psi gauge.

8. The improvement in accordance with claim 1 wherein said catalyst is soluble in the reaction mixture.

9. The improvement in accordance with claim 1 wherein said catalyst is insoluble in the reaction mixture.

10. The improvement in accordance with claim 1 further comprising a secondary promoter reagent, soluble in the reaction mixture, which increases the percent conversion of methanol.

11. The process of claim 10 wherein said promoter agent is an alkali metal halide, alkaline earth halide or $C_1-C_4$ alkyl halide.

12. The process of claim 1 wherein the Group VIII metal catalyst is selected from cobalt-, ruthenium-, rhodium-, or iron-containing salts, or mixtures thereof.

13. The process of claim 12 wherein the catalyst is a cobalt-containing salt.

* * * * *